United States Patent [19]

Asaka et al.

[11] Patent Number: 5,350,839
[45] Date of Patent: Sep. 27, 1994

[54] 2'-POSITION MODIFIED COMPOUND OF ERYTHROMYCIN OR ITS DERIVATIVE

[75] Inventors: Toshifumi Asaka; Yoko Misawa; Masato Kashimura; Shigeo Morimoto, all of Saitama; Yoshiaki Watanabe, Tokyo; Katsuo Hatayama, Saitama, all of Japan

[73] Assignee: Taisho Pharmaceutical Co., Ltd., Tokyo, Japan

[21] Appl. No.: 39,121

[22] PCT Filed: Oct. 8, 1991

[86] PCT No.: PCT/JP91/01368
§ 371 Date: Apr. 15, 1992
§ 102(e) Date: Apr. 15, 1992

[87] PCT Pub. No.: WO92/06991
PCT Pub. Date: Apr. 30, 1992

[51] Int. Cl.$^5$ ............................................. C07H 17/08
[52] U.S. Cl. ........................................ 536/7.4; 536/7.2
[58] Field of Search ................... 514/29; 536/7.2, 7.4

[56] References Cited

U.S. PATENT DOCUMENTS

| 4,382,086 | 5/1983 | Sciavolino et al. | 514/29 |
| 4,668,664 | 5/1987 | Rougier et al. | 514/29 |
| 4,677,097 | 6/1987 | Omura et al. | 514/29 |
| 4,948,782 | 8/1990 | Omura et al. | 514/29 |

Primary Examiner—Johnnie R. Brown
Assistant Examiner—Elli Peselev
Attorney, Agent, or Firm—Oblon, Spivak, McClelland, Maier & Neustadt

[57] ABSTRACT

Erythromycins showing an extremely relieved bitterness at administration and an improved absorbability in vivo when orally administered are provided.

A compound having a group represented by the following formula:

$$-O-CO-O-[(CH_2)_m-O]_n-R$$

(wherein R represents an alkyl group having from 1 to 12 carbon atoms, m represents an integer of from 2 to 4, and n represents an integer of from 1 to 7) at the 2'-position of erythromycins or a salt thereof.

2 Claims, No Drawings

2'-POSITION MODIFIED COMPOUND OF ERYTHROMYCIN OR ITS DERIVATIVE

TECHNICAL FIELD

This invention relates to a 2'-position modified compound of erythromycins. More particularly, it relates to a 2'-position modified compound of erythromycins which shows an extremely relieved bitterness at administration and an improved absorbability in vivo when formulated into a drug.

BACKGROUND ART

In most cases, erythromycins, which are used in chemotherapy for various bacterial infections, are orally administered. When these compounds are to be administered via internal use, the characteristic bitterness thereof makes it necessary to formulate them into capsules or coated tablets. For those who cannot smoothly swallow down these drugs such as children and aged persons, however, it is desirable to formulate these compounds into solutions or granules. In these cases, the bitterness cannot be fully relieved by simply masking them. In order to solve these problems, attempts have been made to develop various esters which show no bitterness at the administration but return into the original active compounds at or after the absorption in vivo.

Examples of these esters include erythromycin ethylsuccinate [Antibiotics and Chemotherapy, 7 (9), 487 (1957)], erythromycin propionate lauryl sulfate [Journal of the American Pharmaceutical Association, .48 (11), 620 (1959)], allyl, ethyl and benzyl carbonates of erythromycin [Antibiotics Annual, 1953–1954, 500 (1954)]and 2'-ester of O-methylerythromycin derivative (JP-A-61-200998).

However these known compounds are generally insufficient in absorbability in vivo. Further, these compounds per se generally have a weak antibacterial activity. Therefore, they should be rapidly converted into the original active compounds in vivo. However, these compounds are hardly converted into the original active compounds in vivo in practice, which makes it impossible to achieve satisfactory therapeutic effects.

DISCLOSURE OF THE INVENTION

Therefore, the present inventors have conducted extensive studies on 2'-modifying groups of various erythromycins and, consequently, found out that a 2'-position modified compound of erythromycins, which shows an extremely relieved bitterness at administration and an improved absorbability in vivo and can rapidly return into the original active compound in vivo, can be obtained by introducing a group represented by the following formula:

$$-O-CO-O-[(CH_2)_m-O]_n-R$$

into erythromycins, thus completing the present invention.

The present invention relates to a compound having a group represented by the following formula (I):

$$-O-CO-O-[(CH_2)_m-O]_n-R \qquad (I)$$

(wherein R represents an alkyl 9group having from 1 to 12 carbon atoms, m represents an integer of from 2 to 4, and n represents an integer of from 1 to 7) at the 2'-position of erythromycins or a salt thereof.

The term "erythromycins" as used herein means compounds having an erythromycin skeleton and those derived from erythromycin. Examples thereof include erythromycin (for example, erythromycin A, erythromycin B), 6-0-methyl-erythromycin A (clarithromycin), erythromycin A 9-{0-[(2-methoxyethoxy)methyl]oxime}(roxithromycin), 9-deoxo-9a-methyl-9a-aza-9a-homoerythromycin A (azithromycin), erythromycin 11, 12-carbonate (davercin), 8-fluoroerythromycin A (flurithromycin), halogen-substituted benzyloxime derivatives of 6-0-methylerythromycin A {for example, 6-0-methylerythromycin A 9-[0-(2,6-difluorobenzyl)oxime], 6-0-methylerythromycin A 9-[0-(4-bromobenzyl)oxime]}, 9-deoxo-11,12-dideoxy-9,12-epoxy-ll-oxo-9,10-didehydro-erythromycin A, 11-amino-9-deoxo-11,12-dideoxy A, 9-deoxo-9-(4,4-dimethyl)piperidino-erythromycin A, 11-deoxy-11-[carboxy-(N-methyl, N-benzyl-aminoethyl)amino]-6-0-methylerythromycin A 11,12-cyclic ester, 4"-deoxyerythromycin A and 4"-deoxyerythromycin A 11,12-cyclic carbonate.

The alkyl group having from 1 to 12 carbon atoms involves straight- or branched-chain groups.

Examples of the salt include those formed with acids such as acetic acid, propionic acid, butyric acid, formic acid, trifluoroacetic acid, maleic acid, fumaric acid, lactic acid, tartaric acid, citric acid, stearic acid, succinic acid, ethylsuccinic acid, lactobionic acid, glycolic acid, glucoheptonic acid, benzoic acid, methanesulfonic acid, ethanesulfonic acid, 2-hydroxyethanesulfonic acid, benzene-sulfonic acid, p-toluenesulfonic acid, lauryl sulfuric acid, malic acid, aspartic acid, glutamic acid, adipic acid, cysteine, N-acetylcysteine, thiomaleic acid, hydrochloric acid, hydrobromic acid, phosphoric acid, sulfuric acid, hydroiodic acid, nicotinic acid, oxalic acid, picric acid, thiocyanic acid, undecanoic acid, acrylate polymer and carboxyvinyl polymer.

Preferable examples of the compound of the present invention are 2'-position modified compounds of erythromycins having a group of the formula (I), wherein m is 2, n is 3 or 4 and R is an alkyl group having from 1 to 3 carbon atoms, at the 2'-position and salts thereof.

The compound according to the present invention can be produced by the following method.

Namely, it can be obtained by reacting a compound which is an erythromycin having a hydroxyl group at the 2'-position with from 1 to 3 equivalents, preferably from 1 to 1.6 equivalents, of a compound represented by the formula:

$$Cl-CO-O-[(CH_2)_m-O]_n-R \qquad (II)$$

(wherein R, m and n are as defined above) in an inert solvent in the presence of a dehydrochlorinating agent.

Examples of the compound of the above formula (II) include 2-ethoxyethyl chloroformate, 2-(2-methoxyethoxy)ethyl chloroformate, 2-(2-ethoxyethoxy)ethyl chloroformate, 2-[2-(2-methoxyethoxy)ethoxy]ethyl chloroformate, 2-[2-(2-ethoxyethoxy)ethoxy]ethyl chloroformate, 2-[2-(2-isopropyloxyethoxy)ethoxy]ethyl chloroformate, 2-{2-[2-(2-methoxyethoxy)ethoxy]ethoxy}ethyl chloroformate, 2-(2-n-butoxyethoxy)ethyl chloroformate, 2-(2-dodecyloxyethoxy)ethyl chloroformate, 2(2-n-hexyloxyethoxy)ethyl chloroformate, 3-(3-methoxypropyl-oxy)propyl chloroformate, 3-[3-(3-methoxypropyloxy) propyl chloroformate, 2-{2-[2-(2-methoxyethoxy)-ethoxy)ethoxy]ethoxy}ethyl chloroformate, 2-{2-[2-(2-(2-methoxyethoxy)ethoxy)ethoxy]ethoxy}ethyl chloroformate and 2-{2-[2-(2-(2-(2-(2-methoxyethoxy)ethoxy)ethoxy)ethoxy)-ethoxy]ethoxy}ethyl chloroformate.

As the above-mentioned dehydrochlorinating agent, sodium hydroxide, potassium hydroxide, sodium hydrogen-carbonate, potassium carbonate, sodium carbonate and triethylamine are usable. These agents may be used in an amount of from 1 to 2 equivalents, preferably from 1.1 to 1.3 equivalents (in the case of sodium hydroxide and potassium hydroxide), from 3 to 8 equivalents, preferably 5 equivalents (in the case of sodium hydrogencarbonate, potassium carbonate and sodium carbonate) and from 1 to 5 equivalents, preferably 3 equivalents (in the case of triethylamine), each based on the erythromycin having a hydroxyl group at the 2'-position and the compound of the formula (II).

As the above-mentioned inert solvent, acetone, ethyl acetate, dichloromethane, chloroform, toluene, ether and tetrahydrofuran are usable. It is preferable to use acetone, ethyl acetate, dichloromethane or tetrahydrofuran therefor.

The reaction time may usually range from 30 minutes to 4 hours at ambient temperature, though a longer reaction time is needed when the reaction proceeds slowly, When the reaction cannot sufficiently proceed, the dehydrochlorinating agent and the compound of the formula (II) may be further added, followed by continuing the reaction.

BEST MODE FOR EMBODYING THE INVENTION

To further illustrate the present invention in greater detail, the following Examples and Test Example will be given.

EXAMPLE 1

To a solution of 6-O-methylerythromycin A (20 g) in tetrahydrofuran (80 ml), were added 2-ethoxyethyl chloro-formate (4.9 g) and 85% potassium hydroxide powder (2.12 g), followed by stirring at room temperature for 3.5 hours. Then, the reaction mixture was poured into water and extracted with ethyl acetate. The ethyl acetate layer was washed with a saturated solution of sodium hydrogencarbonate and dried over anhydrous magnesium sulfate.

After distilling off the solvent under reduced pressure, the crude product thus obtained was purified by silica gel column chromatography (elution solvent; acetone: chloroform =1: 2) to thereby give 6-O-methylerythromycin A 2'-(2-ethoxyethyl) carbonate (18.4 g). Then, the product was recrystallized from dichloromethane/petroleum ether.

m.p.: 204°–206 ° C.

$^1$H-NMR (CDCl$_3$) δppm: 2.30 (6H, s), 3.03 (3H, s), 3.35 (3H, s), 3.50–3.69 (6H, m)

EXAMPLE 2

To a solution of 6-O-methylerythromycin A (20 g) in tetrahydrofuran (80 ml), were added 3-[3-(3-methoxypropyl-oxy)propyloxy]propyl chloroformate (8.63 g) and 85% potassium hydroxide powder (2.12 g), followed by stirring at room temperature for 4.5 hours. Then, the same treatment as the one described in Example 1 was performed. After recrystallizing from dichloromethane/n-hexane, 6-O-methyl-erythromycin A 2'-{3-[3-(3-methoxypropyloxy)propyloxy]propyl}carbonate was obtained in the form of a white powder (12.8 g).

m.p.: 79°–85 ° C.

$^1$H-NMR (CDCl$_3$) δppm: 2.32 (6H, s), 3.02 (3H, s), 3.34 (3H, s), 3.37 (3H, s).

EXAMPLE 3

To a solution of 6-0-methylerythromycin A (20 g) in tetrahydrofuran (80 ml), were added 2-[2-(2-methoxyethoxy)-ethoxy] ethyl chloroformate (6.97 g) and 95% potassium hydroxide powder (1.82 g), followed by stirring at room temperature for 3 hours. After distilling off the most part of the reaction solvent under reduced pressure, ethyl acetate (100 ml) was added to the residue. The ethyl acetate solution was washed with a saturated aqueous solution of common salt (100 ml) twice and concentrated under reduced pressure. The colorless, foamy substance thus obtained was purified by silica gel column chromatography (elution solvent; acetone: chloroform =2 : 25 - 1 : 2) and crystallized from chloroform/n-hexane. Thus 6-O-methylerythromycin A 2'-{2-[2-(2-methoxyethoxy)ethoxy]ethyl}carbonate was obtained in the form of a white powder (11.2 g).

m.p.: 159°–160 ° C.

$^1$H-NMR (CDCl$_3$)δppm: 2.28 (6H, s), 3.02 (3H, s), 3.35 (3H, s), 3.39 (3H, s).

EXAMPLE 4

To a solution of 6-0-methylerythromycin A (20 g) in tetrahydrofuran (60 ml), were added 95% potassium hydroxide powder (1.9 g) and 2-(2-n-hexyloxyethoxy)ethyl chloroformate (8.1 g). The resulting mixture was stirred at room temperature for 4 hours and then allowed to stand overnight. After filtering off the insoluble matters, the filtrate was concentrated under reduced pressure. The foamy substance thus obtained was purified by silica gel column chromatography (elution solvent; methanol : chloroform =1 :99–3: 97) to thereby give 6-O-methylerythromycin A 2'-[2-(2 -n-hexyloxyethoxy)ethyl]carbonate (16.03 g) in the form of a colorless foamy substance. After recrystallizing from petroleum ether, 14.12 g of a white powder was obtained.

m.p.:92°–94° C.

$^1$H-NMR (CDCl$_3$) δppm: 2.28 (6H, s), 3.02 (3H, s), 3.35 (3H, s).

EXAMPLE 5

To a solution of erythromycin A (22 02 g) in tetrahydrofuran, were added 85% potassium hydroxide powder (2.57 g) and 2-[2-(2-methoxyethoxy)ethoxy]ethyl chloroformate (10.2 ml). The resulting mixture was stirred at room temperature for 3.5 hours and then allowed to stand overnight. Then ethyl acetate (500 ml), a saturated solution of sodium hydrogencarbonate (500 ml) and triethylamine (10 ml) were added to the reaction mixture. The ethyl acetate layer was separated, washed with water and concentrated to thereby give a foamy substance (27.5 g). 24.9 g of this foamy product was purified by silica gel column chromatography (elution solvent; acetone: chloroform =1 : 8 - 1 : 4) to thereby give erythromycin A 2 '-{2-[2-(2-methoxyethoxy)ethoxy]ethyl}carbonate (6.7 g) in the form of a colorless foamy substance.

$^1$H-NMR (CDCl$_3$) δppm: 3.32 (6H, s), 3.33 (3H, s), 3.39 (3H, s).

EXAMPLE 6

To a solution of 6-O-methylerythromycin A (20 g) in tetrahydrofuran (60 ml), were added 2-(2-n-butoxyethoxy)ethyl chloroformate (7.21 g) and 95% potassium hydroxide powder (1.9 g), followed by stirring at room temperature for 2 hours. Then, the same treatment as the one described in Example 3 was performed. The crude product thus obtained was purified by silica gel column chromatography (elution solvent; methanol : chloroform =2 : 98 - 3 : 97) and then crystallized from petroleum ether to thereby give 6-O-methylerythromycin A 2'-[2-(2-n-butoxyethoxy)ethyl]carbonate (14.85 g) in the form of a white powder.

m.p.: 134°–136 ° C.

$^1$H-NMR (CDCl$_3$) δppm: 2.29 (6H, s), 3.02 (3H, s), 3.35 (3H, s).

EXAMPLE 7

To a solution of 6-0-methylerythromycin A (9.25 g) in tetrahydrofuran (90 ml), were added 2-(2-dodecyloxyethoxy)-ethyl chloroformate (5 g) and 95% potassium hydroxide powder (0.877 g), and the resulting mixture was stirred at room temperature for 30 minutes. Then, ethyl acetate (200 ml) and a saturated aqueous solution of common salt (200 ml) were added to the reaction mixture and thoroughly stirred. The ethyl acetate layer was separated, washed with a saturated aqueous solution of common salt (200 ml) and dried over anhydrous magnesium sulfate.

After distilling off the solvent under reduced pressure, the residue thus obtained was purified by silica gel column chromatography (elution solvent; acetone: n-hexane: triethylamine =3 : 10 : 0.2) and then crystallized from petroleum ether. Thus 6-0-methylerythromycin A 2'-[2(2-dodecyloxyethoxy)ethyl]carbonate (9.49 g) was obtained.

m.p.: 106°–108 ° C.

$^1$H-NMR (CDCl$_3$) δppm: 2.28 (6H, s), 3.02 (3H, s), 3.32 (3H, s).

EXAMPLE 8

To a solution of 6-0-methylerythromycin (10 g) in tetrahydrofuran (60 ml), were added 3-(3-methoxypropyloxy)-propyl chloroformate (3.38 g) and 85 % potassium hydroxide powder (1.06 g), and the resulting mixture was stirred at room temperature for 30 minutes. Then, it was treated by the same method as the one described in Example 7. The crude product thus obtained was purified by silica gel column chromatography (elution solvent; acetone: benzene =1 : 4) and then crystallized from dichloromethane/isopropyl ether. Thus 6-O-methylerythromycin A 2'-[3-(3-meth6xypropyloxy)propyl]carbonate (9.86 g) was obtained.

m.p.: 147°–149 ° C.

$^1$H-NMR (CDCl$_3$) δppm: 2.28 (6H, d), 3.02 (3H, s), 3.35 (3H, s).

EXAMPLE 9

To a solution of erythromycin A 9-{0-[(2-methoxyethoxy)methyl]oxime (1 g) in tetrahydrofuran (5 ml), were added 2-(2-n-butoxyethoxy)ethyl chloroformate (0.322 g) and 85% potassium hydroxide powder (0.095 g), and the resulting mixture was stirred at room temperature for 20 minutes. Then, it was treated by the same method as the one described in Example 7. The crude product thus obtained was purified by silica gel column chromatography (elution solvent; acetone :benzene =1: 4). Thus erythromycin A 9-{0-[(2-methoxyethoxy)methyl]oxime}2'-[2-(2-n-butoxyethoxy)ethyl]-carbonate (0.95 g) was obtained.

$^1$H-NMR (CDCl$_3$) δppm: 2.31 (6H, s).

EXAMPLE 10

To a solution of erythromycin B (1 g) in tetrahydrofuran (5 ml), were added 2-[2-(2-methoxyethoxy)ethoxy]ethyl chloroformate (0.379 g) and 85% potassium hydroxide powder (0.11 g), and the resulting mixture was stirred at room temperature for 1 hour. Then, 2-[2-(2-methoxyethoxy)ethoxy]-ethyl chloroformate (0.126 g) and 85% potassium hydroxide powder (0.037 g) were further added thereto, followed by stirring for additional 30 minutes. Next, it was treated by the same method as the one described in Example 7. The crude product thus obtained was purified by silica gel column chromatography (elution solvent; acetone: chloroform =1 : 1) and then crystallized from ethyl acetate/hexane. Thus erythromycin B 2'-{2-[2-(2-methoxyethoxy)ethoxy]ethyl}carbonate (0.9 g) was obtained.

m.p.: 80°–81 ° C.

$^1$H-NMR (CDCl$_3$) δppm: 2.31 (6H, s), 3.34 (3H, s), 3.39 (3H, s).

EXAMPLE 11

To a solution of 9-deoxo-9a-aza-9a-methyl-9a-homoerythromycin A (1.49 g) in acetone (20 ml), were added 2-[2-(2-methoxyethoxy)ethoxy]ethyl chloroformate (0.544 g) and sodium hydrogencarbonate (0.84 g), and the resulting mixture was stirred at room temperature for 4 hours.

After distilling off most of the acetone under reduced pressure, water was added to the residue which was then extracted with ethyl acetate. The ethyl acetate layer was washed with a saturated solution of sodium hydrogen-carbonate, dried over anhydrous magnesium sulfate and then concentrated under reduced pressure. The residue was purified by silica gel column chromatography (elution solvent; acetone : chloroform =1 : 2). Thus 9-deoxo-9a-aza-9a-methyl-9a-homoerythromycin A 2'-ethyl}carbonate (1.4 g) was obtained as a pale yellow, foamy substance.

m.p.: 68°–71 ° C.

$^1$H-NMR (CDCl$_3$) δppm: 2.30 (6H, 2.38 (3H, s), 3.35 (3H, s), 3.39 (3H, s).

EXAMPLE 12

6-O-Methylerythromycin A (2.24 g) was dissolved in a solvent mixture comprising acetone (30 ml) and dichloro-methane (10 ml). After adding sodium hydrogencarbonate (1.26 g) and 2-(2-methoxyethoxy)ethyl chloroformate (0.657 g), the mixture was stirred at room temperature for 4 hours. Then, the reaction mixture was poured into water and extracted with dichloromethane.

The dichloromethane layer was washed with a saturated solution of sodium hydrogencarbonate, dried over anhydrous magnesium sulfate and then concentrated under reduced pressure. The residue thus obtained was purified by silica gel column chromatography (elution solvent; acetone: chloroform =1 : 3 - 1 : 2). Thus 6-O-methylerythromycin A 2'-[2-(2-methoxyethoxy)ethyl]-carbonate (2 g) was obtained as a colorless, foamy substance. Then, this product was recrystallized from dichloromethane/petroleum ether.

m.p.: 203°–205 ° C.

$^1$H-NMR (CDCl$_3$) δppm: 2.28 (6H, s), 3.01 (3H, s), 3.35 (3H, s), 3.40 (3H, s).

EXAMPLE 13

To a solution of 6-0-methylerythromycin A (2.24 g) in dichloromethane (30 ml), were added sodium hydrogencarbonate (1.26 g) and 2-(2-ethoxyethoxy)ethyl chloroformate (0.63 ml) under ice-cooling. Then, the resulting mixture was stirred at room temperature for 5.5 hours. Subsequently, it was treated by the same method as the one described in Example 12. Thus 6-O-methylerythromycin A 2'-[2-(2-ethoxyethoxy)ethyl]-carbonate (1.81 g) was obtained as a white powder. Then, it was recrystallized from dichloromethane/isopropyl ether.

m.p.: 191°–193 °C.

$^1$H-NMR (CDCl$_3$) δppm: 2.27 (6H, s), 3.01 (3H, s), 3.35 (3H, s).

EXAMPLE 14

To a solution of 6-O-methylerythromycin A (10 g) in tetrahydrofuran (50 ml), were added 95 % potassium hydroxide powder (0.87 g) and 2 - [2 - ( 2 -ethoxyethoxy ) ethoxy ]ethyl chloroformate (3.60 g) under ice-cooling. After stirring for 3 hours, 95% potassium hydroxide powder (0.24 g) and 2- [2-( 2 -ethoxyethoxy ) ethoxy ]ethyl chloroformate ( 0.98 g ) were further added thereto and the mixture was stirred for additional 2 days. The post treatment was performed by the same method as the one described in Example 7. The crude product thus obtained was purified by silica gel column chromatography (elution solvent; acetone : n-hexane =7 : 13 - 2 : 3) and then crystallized from chloroform/n-hexane. Thus 6-0-methylerythromycin A 2 '- {2- [2- ( 2-ethoxyethoxy ) ethoxy]ethyl}carbonate (8.85 g) was obtained as a white powder.

m.p.: 91°–93 °C.

$^1$H-NMR (CDCl$_3$) δppm: 2.30 (6H, s), 3.01 (3H, s), 3.34 (3H, s).

EXAMPLE 15

To a solution of 6-O-methylerythromycin A (10 g) in tetrahydrofuran (50 ml), were added 95% potassium hydroxide powder (0 87 g) and 2-{2-[2-(2-methoxyethoxy)ethoxy]ethoxy}-ethyl chloroformate (3.98 g) under ice-cooling. After stirring for 5 hours, 95 % potassium hydroxide powder (1.08 g) and 2-{2-[2-( 2-methoxyethoxy)ethoxy]ethoxy}ethyl chloroformate (0.24 g) were further added thereto and the mixture was stirred for 4 hours under ice-cooling. After allowing to react at room temperature for additional 15 hours, the post treatment was performed by the same method as the one described in Example 7. The crude product thus obtained was purified by silica gel column chromatography (elution solvent; acetone: chloroform =1 : 5 - 2 : 5 ) and then crystallized from chloroform/n-hexane. Thus 6-O-methylerythromycin A 2'-{2-[2-(2-(2-methoxyethoxy)ethoxy]ethyl}carbonate (8.44 g) was obtained as a white powder.

m.p.: 81°–83 °C.

$^1$H-NMR (CDC13) δppm: 2 26 (6H, s), 2 99 (3H, s), 3.32 (3H, s), 3.36 (3H, s).

EXAMPLE 16

To a solution of 6-0-methylerythromycin A (10 g) in tetrahydrofuran (50 ml), were added 95% potassium hydroxide powder (0.95 g) and 2-[2-(2-isopropyloxyethoxy)ethoxy]ethyl chloroformate (4.09 g) under ice-cooling. After stirring at the same temperature for 1 hour, the mixture was returned to room temperature and then further stirred for 20 hours. The post treatment, isolation and purification were performed by the same method as the one described in Example 15. Thus 6-O -methylerythromycin A 2'-{2-[2-(2-isopropyloxyethoxy)ethoxy]ethyl}carbonate (5.85 g) was obtained as a white powder.

m.p.: 69°–71 °C.

$^1$H-NMR (CDCl$_3$) δppm: 2..26 (6H, s), 2.99 (3H, s), 3.32 (3H, s).

EXAMPLE 17

To a solution of 6-O-methylerythromycin A (50 g) in ethyl acetate (400 ml), were added triethylamine (17.34 ml) and 2-[2-(2-methoxyethoxy)ethoxy]ethyl chloroformate (22.73 g) under ice-cooling. After stirring at the same temperature for 3 hours, the mixture was returned to room temperature and then further stirred for 1 day. Then, triethylamine (8.67 ml) and 2-[2-(2-methoxyethoxy)ethoxy]ethyl chloroformate (15.15 g) were further added thereto at room temperature and the mixture was stirred for additional 1 day. Then, water (300 ml) and a saturated aqueous solution of common salt (100 ml) were added to the reaction mixture. The ethyl acetate layer obtained by separating was washed with a saturated aqueous solution of common salt (300 ml) twice and dried over anhydrous magnesium sulfate, followed by distilling off the solvent under reduced pressure.

To the residue thus obtained, was added ethyl acetate (70 ml). After dissolving, petroleum ether (300 ml) was poured therein to thereby give 6-0-methylerythromycin A 2'-{2-[2-(2-methoxyethoxy)ethoxy]ethyl}carbonate (59.94 g), i.e., the same product as the one obtained in Example 3, as a white powder.

EXAMPLE 18

To a solution of 6-O-methylerythromycin A (3.74 g) in ethyl acetate (40 ml), were added at room temperature triethylamine (3.89 ml) and then 2-{2-[2-(2-(2-methoxy-ethoxy)ethoxy)ethoxy]ethoxy}ethyl chloroformate (6.30 g), followed by stirring for 20 hours. Then, the resulting mixture was treated by the same method as the one described in Example 1. Thus yellow crystals (5.12 g) of 6-0-methyl-erythromycin A 2'-{2-[2-(2-(2-(2-methoxyethoxy)ethoxy)ethoxy)ethoxy]ethyl} carbonate were obtained.

m.p.: 81°–83 °C.

$^1$H-NMR (CDCl$_3$) δppm: 2.40 (6H, br. s), 3.01 (3H, s), 3.34 (3H, s), 3.38 (3H, s).

EXAMPLE 19

To a solution of 6-O-methylerythromycin A (3.74 g) in ethyl acetate (40 ml), were added at room temperature triethylamine (3.89 ml) and then 2-{2-[2-(2-(2-(2-methoxy-ethoxy)ethoxy)ethoxy)ethoxy]ethoxy}ethyl chloroformate (7.18 g), followed by stirring for 20 hours. Then, the resulting mixture was treated by the same method as the one described in Example 1. Thus colorless crystals (4.60 g) of 6—0—methylerythromycin A 2'-{2-[2-(2-(2-(2-(2-methoxyethoxy)ethoxy)ethoxy)ethoxy)ethoxy]ethyl}carbonate were obtained.

m.p.: 55°–57 °C.

$^1$H-NMR (CDCl$_3$) δppm: 2.36 (6H, br. s), 3.01 (3H, s), 3.34 (3H, s), 3.38 (3H, s).

EXAMPLE 20

To a solution of 6-O-methylerythromycin A 9-[0-(4bromobenzyl)oxime](1.86 g) in ethyl acetate (20 ml), were added at room temperature triethylamine (1.04 ml) and then 2[2-(2-methoxyethoxy)ethoxy]ethyl chloroformate (0.91 g), followed by stirring for 1 day. Then, the resulting mixture was treated by the same method as the one described in Example 1. Thus 6-O-methylerythromycin A 9- [O- ( 4-bromo-benzyl) oxime ]2'-{2-[2-( 2-methoxyethoxy)ethoxy]ethyl }carbonate was obtained as a colorless, foamy substance (970 mg) .

$^1$H-NMR (CDCl$_3$) δppm: 2.30 (6H, s), 3.02 (3H, s), 3.34 (3H, s), 3.38 (3H, s).

EXAMPLE 21

To a solution of 6-0-methylerythromycin A 9-[O-(2,6-difluorobenzyl)oxime](1.78 g) in ethyl acetate, were added at room temperature triethylamine (1.04 ml) and then 2-[2-(2-methoxyethoxy)ethoxy]ethyl chloroformate (1.36 g), followed by stirring over day and night. Then, the resulting mixture was treated by the same method as the one described in Example 1. Thus 6-0-methylerythromycin A 9-[O-(2,6-difluoro-benzyl) oxime]2'-{2-[2-(2-methoxyethoxy)ethoxy]ethyl}carbonate was obtained as a colorless, foamy substance (1.05 g).

$^1$H-NMR (CDCl$_3$) δppm: 2 31 (6H, s), 2 87 (3H, s), 3.33 (3H, s), 3.78 (3H, s).

TEST EXAMPLE

The compounds of the present invention (samples 1 to 6) and known esters of macrolide compounds (control samples 1 to 4), which were employed as a control, were each suspended in a 5% aqueous solution of gum arabic and orally administered to male ICR mice (each group having 12 animals) in a dose of 100 mg/kg. Then, 3 portions of the mice were killed by bloodletting at intervals of a definite period and the antibacterial activities in the serum were determined. The antibacterial activities were determined by the paper disc method with the use of Micrococcus luteus ATCC 9341 as a test strain.

Table 1 summarizes the results.

TABLE 1

| Sample | Antibacterial Activity in Serum (μg/ml) | | | |
| --- | --- | --- | --- | --- |
|  | After 30 min. | After 1 hr. | After 2 hr. | After 4 hr. |
| Sample 1 | 11.02 | 7.37 | 5.46 | 1.96 |
| Sample 2 | 9.07 | 5.87 | 2.94 | 1.40 |
| Sample 3 | 10.20 | 9.14 | 3.04 | 0.83 |

TABLE 1-continued

| Sample | Antibacterial Activity in Serum (μg/ml) | | | |
| --- | --- | --- | --- | --- |
|  | After 30 min. | After 1 hr. | After 2 hr. | After 4 hr. |
| Sample 4 | 19.89 | 9.54 | 4.20 | 2.87 |
| Control 1 | 0.64 | 0.30 | 0.63 | 1.44 |
| Control 2 | 0.86 | 0.63 | 0.59 | 0.26 |
| Control 3 | 0.05 | 0.03 | 0.26 | 0.20 |
| Sample 5 | 2.63 | 3.00 | 1.79 | 0.02 |
| Control 4 | 0.31 | 0.31 | 0.15 | 0.02 |
| Sample 6 | 7.21 | 10.98 | 10.01 | 5.62 |

Sample 1: the compound produced in Example 3.
Sample 2: the compound produced in Example 13.
Sample 3: the compound produced in Example 14.
Sample 4: the compound produced in Example 15.
Sample 5: the compound produced in Example 5.
Sample 6: the compound produced in Example 11.
Control sample 1: 6-O-methylerythromycin A 2'-ethylsuccinate.
Control sample 2: 6-O-methylerythromycin A 2'-ethylcarbonate.
Control sample 3: 6-O-methylerythromycin A 2'-benzylcarbonate.
Control sample 4: erythromycin A 2'-ethylcarbonate.

INDUSTRIAL APPLICABILITY

According to the present invention, it becomes possible to provide a 2'-position modified compound of erythromycins which shows an extremely relieved bitterness at administration and an improved absorbability in vivo when orally administered.

What is claimed is:

1. A compound having a group represented by the following formula (I):

wherein R represents an alkyl group having from 1 to 12 carbon atoms, m represents an integer of from 2 to 4, and n represents an integer of from 1 to 7, at the 2'-position of an erythromycin or a pharmaceutically acceptable salt thereof.

2. A compound as claimed in claim 1 wherein said erythromycin is erythromycin A, erythromycin B, clarithromycin, roxithromycin, azithromycin, davercin, flurithromycin, 6-0-methylerythromycin A 9-[O-(2,6-difluorobenzyl)oxime], 6-0-methylerythromycin A 9-[O-(4-bromobenzyl)oxime], 9-deoxo-ll,12-dideoxy-9,12-epoxy-11-oxo-9,10didehydroerythromycin A, 11-amino-9-deoxo-11,12-dideoxy-9,12epoxyerythromycin A, 9-deoxo-9-(4,4-dimethyl)piperidinoerythromycin A, 11-deoxy-11-[carboxy-(N-methyl, N-benzy! aminoethyl)amino]-6-0-methylerythromycin A 11,12-cyclic ester, 4"-deoxyerythromycin A or 4"-deoxyerythromycin A 11,12-cyclic carbonate, or a pharmaceutically acceptable salt thereof.

* * * * *

UNITED STATES PATENT AND TRADEMARK OFFICE
CERTIFICATE OF CORRECTION

PATENT NO. : 5,350,839
DATED : September 27, 1994
INVENTOR(S) : Toshifumi ASAKA, et al.

It is certified that error appears in the above-indentified patent and that said Letters Patent is hereby corrected as shown below:

On the Title Page, Item [86], the §371 Date and §102(e) Date should read as follows:

--Apr. 15, 1993--

Signed and Sealed this

Twenty-seventh Day of December, 1994

Attest:

BRUCE LEHMAN

Attesting Officer

Commissioner of Patents and Trademarks